United States Patent
Bengtsson et al.

(10) Patent No.: US 11,426,632 B2
(45) Date of Patent: Aug. 30, 2022

(54) DEVICE AND METHOD FOR ENHANCING USER OPERATION OF AN EXERCISE MACHINE

(71) Applicant: SONY CORPORATION, Tokyo (JP)

(72) Inventors: Henrik Bengtsson, Lund (SE); Jakob Håkansson, Lund (SE)

(73) Assignee: SONY CORPORATION, Tokyo (JP)

( * ) Notice: Subject to any disclaimer, the term of this patent is extended or adjusted under 35 U.S.C. 154(b) by 202 days.

(21) Appl. No.: 16/785,589

(22) Filed: Feb. 8, 2020

(65) Prior Publication Data
US 2020/0316434 A1  Oct. 8, 2020

(30) Foreign Application Priority Data

Apr. 2, 2019  (SE) .................................. 1950404-2

(51) Int. Cl.
*A63B 24/00* (2006.01)
*A63B 71/06* (2006.01)
*A63B 21/062* (2006.01)

(52) U.S. Cl.
CPC ...... *A63B 24/0075* (2013.01); *A63B 21/0628* (2015.10); *A63B 24/0062* (2013.01); *A63B 24/0087* (2013.01); *A63B 71/0622* (2013.01); *A63B 71/0686* (2013.01); *A63B 2220/30* (2013.01); *A63B 2220/833* (2013.01); *A63B 2225/52* (2013.01)

(58) Field of Classification Search
None
See application file for complete search history.

(56) References Cited

U.S. PATENT DOCUMENTS

| | | | |
|---|---|---|---|
| 2006/0264299 A1* | 11/2006 | Farinelli | A63B 24/0006 482/8 |
| 2007/0224582 A1* | 9/2007 | Hayashino | A63B 21/0058 434/247 |
| 2011/0077127 A1* | 3/2011 | Ishii | A63B 21/0058 482/8 |
| 2012/0142497 A1 | 6/2012 | Ishii et al. | |
| 2014/0113261 A1 | 4/2014 | Akiba | |
| 2016/0346617 A1* | 12/2016 | Srugo | A63B 21/072 |

FOREIGN PATENT DOCUMENTS

| | | |
|---|---|---|
| WO | 2007060616 A2 | 5/2007 |
| WO | 2015/113162 A1 | 8/2015 |

OTHER PUBLICATIONS

Swedish Search Report and Office Action from corresponding Swedish Patent Application No. 1950404-2, dated Oct. 14, 2019, 9 pages.

* cited by examiner

*Primary Examiner* — Sundhara M Ganesan
*Assistant Examiner* — Shila Jalalzadeh Abyaneh
(74) *Attorney, Agent, or Firm* — Tucker Ellis LLP (57) ABSTRACT

A device configured to enhance user operation of an exercise machine. The device includes control circuitry including logic configured to obtain a stroke measure associated with an exercise motion performed by the user operating the exercise machine; obtain a speed value associated with a target speed for the exercise motion; determine a target period for the exercise motion, based on the stroke measure and the speed value; and output a guide indicator representing the target period on a display.

15 Claims, 7 Drawing Sheets

DEVICE AND METHOD FOR ENHANCING USER OPERATION OF AN EXERCISE MACHINE

RELATED APPLICATION DATA

This application claims the benefit of Swedish Patent Application No. 1950404-2, filed Apr. 2, 2019, the disclosure of which is incorporated herein by reference in its entirety.

TECHNICAL FIELD

The invention relates generally to devices, systems and methods for measuring, transmitting, recording and displaying information relating to physical exercise. More particularly, solutions are provided for devices and methods for enhancing user operation of an exercise machine, devised for performing an exercise motion, specifically the type of exercise machine that comprises a user-operable movable member having a resistance element, such as a lifting mechanism for selectively engaging a number of weights.

BACKGROUND

In recent years, there has been a virtual explosion in the popularity of exercise and physical fitness. There are many popular forms of physical exercise including, for example, running, cycling, and weight training. The growing interest in weight training is reflected by the growing number of gyms found in both public and private settings.

There are various types of weight training equipment. Typical weight machines, for example, use gravity as the primary source of resistance. A combination of simple machines (e.g., pulleys, levers, wheels, inclines, etc.) to change the mechanical advantage of the overall machine relative to the weight and convey the resistance to the person using the exercise machine. Conventional stacked weight machines, such as those made by Cybex International, Inc. and Nautilus, Inc., typically include a stack of rectangular weight plates through which a lifting mechanism, for example comprising a vertical lifting bar, passes. The lifting bar includes a plurality of holes configured to accept an engaging member, such as a pin. Each of the plates has a corresponding channel that aligns with one of the holes in the lifting bar when the lifting bar is in the lowered or at-rest position. To lift a selected number of the plates, the user operates the engaging member, for example by inserting a pin through the channel and the corresponding hole in the lift bar at a selected weight level. As the user goes through the exercise motion, the lift bar rises, and the engaging member supports all of the plates stacked above it. The various settings on the weight machine allow the user to select from several different levels of resistance over the same range of motion by simply inserting the pin into the lift bar at a desired weight level. Conventional weight pins usually include a cylindrical shaft made of stainless steel or other hard metal. In its simplest form, a weight pin can be made from a single piece of cylindrical metal rod that is bent slightly at one end to form a handle for inserting and removing the pin into a weight stack. Other types of weight pins can include a plastic or metal handle portion that is attached to the cylindrical shaft which is inserted into the weight stack. The shaft can include spring-loaded ball bearings and/or other locking features to releasable engage the pin with the weight stack and prevent it from becoming dislodged during use of the weight machine. Some pins with locking features include a push button on the handle to facilitate engagement of the locking feature with the weight stack and/or lifting bar.

Other types of weight machines employ rotation about a horizontal axis, in which operation to turn a member about the axis, by for example pushing or pulling a lever, is counter-acted by a resistance member including a radially extending member to which variable weight, and/or variable radial length, may be selected. Other alternative types of exercise machines may include other types of resistance members than weight, such as a resilient member, for example a spring mechanism or a rubber band arrangement, which may be stretched or compressed by a user operating a handle or similar member of the machine.

One important aspect of any type of exercise machine is that it is used in a way that is suitable for the intended use. This may of course apply to safety reasons, but also to the optimum way of performing the exercise for a user dependent on the need or wish of the user, or the result the user is aiming for. One shortcoming of conventional weight machines, however, is that they lack a convenient way for the user to track and record his or her progress on a particular machine or group of machines during a particular exercise session or over a given period of time. As a result, people engaged in weight training programs often rely on memory to keep track of how many weights they lifted on a particular occasion, or how many repetitions they performed on a particular machine. Rather than rely on memory, some people use notebooks to manually record information about their workout. Neither of these approaches, however, is particularly convenient.

In this context, a system for tracking workout related information was suggested in WO2015/113162A1. That system includes a wearable device wirelessly connectable to receive workout information related to use of a workout equipment, including a weight being used in the workout equipment. Workout information is collected by means of a weight stack selector device, which may determine both selected weight information and repetition information based on distance measured from a weight stack selector device to a stationary reference point. This may be accomplished by means of a transmitter incorporated in the selector device.

A problem related to systems for measuring and tracking workout data is that the data may still be static and will not guide the user how to perform the exercise. Specifically, exercise machine users often perform the exercise motion too quickly or too slowly. Generally speaking, the speed of the exercise may vary, depending on which type of muscle performance you are aiming to develop or train. For this purpose, users of exercise machines may still need assistance to guide or help them do the movement accurately. An appropriate speed or rate of performing the motion may for example be set by assistance from a personal trainer at the gym. However, it may still be hard to recall and repeat an appropriate speed of motion for a user.

A problem generally associated with systems and methods for tracking, controlling and enhancing user performance in exercise machines is power consumption. In a gym, exercise machines are typically spread out on the floor throughout one or more rooms, and access to a mains outlet is rarely available at each machine. In various embodiments, the system is therefore battery-charged, and moderate power consumption is consequently an overall objective. Furthermore, even if an exercise machine is intended to be used in a certain manner, gym users tend to find new ways of exercising using such machines. The system should be so devised that minimum user interaction is required, and such that accidental tampering or inhibition of the measurement is prevented during foreseeable use of the exercise machine.

SUMMARY

A solution that can assist users to control the exercise machines appropriately, such that a desired effect of the training may be accomplished, is desirable. Moreover, a solution where old exercise machines can be kept and the digitization can be retrofit, and which does not require AC power is what many gyms and machine vendors strive for. An object of embodiments herein is thus to provide solutions for devices and methods for enhancing user operation of an exercise machine, and which is also robust, easy to install, power efficient and that provides a good user experience for users.

According to a first aspect 1, a device is provided, configured to enhance user operation of an exercise machine, comprising
control circuitry including logic configured to
obtain a stroke measure associated with an exercise motion performed by the user operating the exercise machine;
obtain a speed value associated with a target speed for the exercise motion;
determine a target period for the exercise motion, based on the stroke measure and the speed value;
output a guide indicator representing the target period on a display.

A typical speed for a standard motion of a standard machine exercise, for example leg press, can be a speed v, such as 0.3 m/s. With an animation provided on a display that indicates a certain nominal tempo or period, it may be difficult to use the correct, or desired speed in the exercise. Different length of arms or legs for two different users will, with the same animation, create different speeds. By means of the suggested solution, a way to set the cycle time of the animation so that the speed gets to be correct is obtained.

According to a second aspect, a method is provided to be carried out in a user device, including the steps of
obtaining a stroke measure associated with an exercise motion performed by the user operating the exercise machine;
obtaining a speed value associated with a target speed for the exercise motion;
determining a target period for the exercise motion, based on the stroke measure and the speed value;
outputting a guide indicator representing the target period on a display.

According to a third aspect, a system is provided, configured to enhance user operation of an exercise machine, comprising
a device as indicated in the first aspect; and
a sensor arrangement connectable to the exercise machine, including
an accelerometer to sense acceleration during an exercise motion, and
a range meter to sense a relative position of a member of the exercise machine; and
a sensor controller configured to output data based on sensed data to the device.

Various embodiments related to these aspects are set out in the claims.

DETAILED DESCRIPTION

Embodiments will now be described with reference to the drawings, wherein like reference numerals are used to refer to like elements throughout. It will be understood that the figures are not necessarily to scale. Also, features that are described and/or illustrated with respect to one embodiment may be used in the same way or in a similar way in one or more other embodiments and/or in combination with or instead of the features of the other embodiments.

Initially, a setup of a system of devices associated with measuring, communicating and presenting information related to an exercise motion carried out by a user on an exercise machine will be discussed.

Figure 1A:
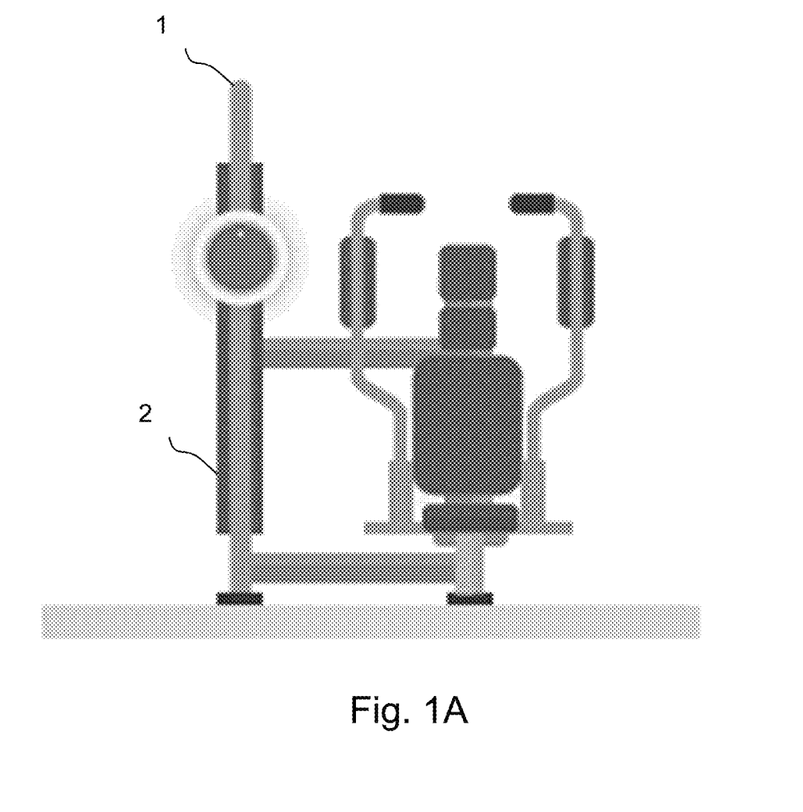
FIGS. 1A and 1B illustrates an exercise machine 1 that may be operated in accordance with the embodiments provided herein.
Figure 1B:
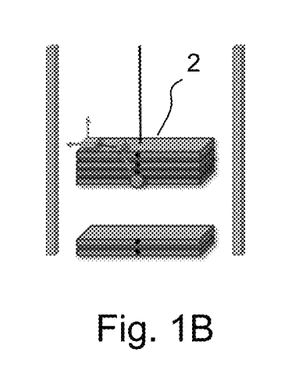

FIG. 1A is an isometric view of a stacked weight exercise machine 1 having a plurality of weights 2 which may be monitored using the proposed monitoring system. In FIG. 1B the stacked weights are shown in further detail.

Figure 2A:
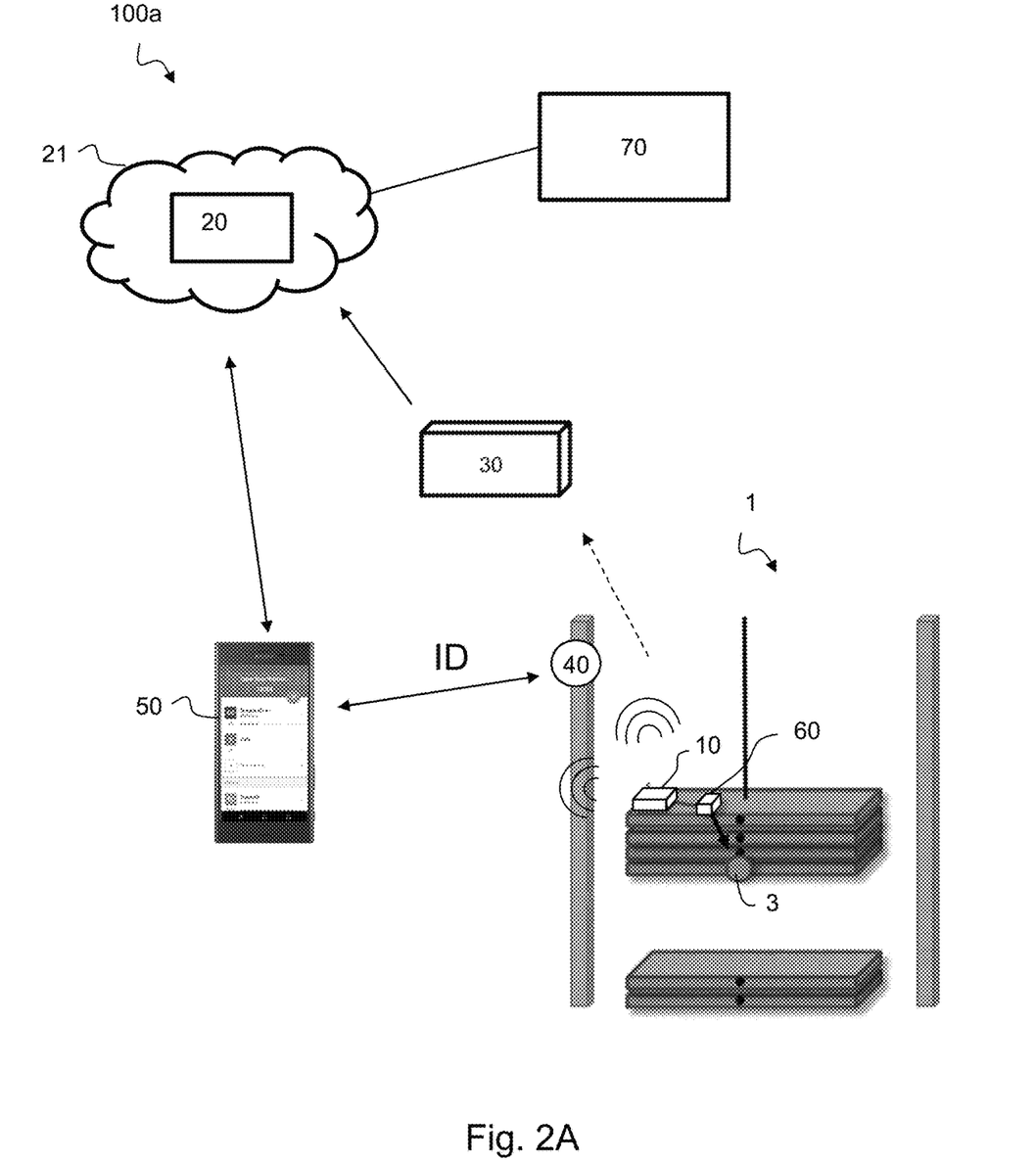
FIG. 2A illustrates a first example embodiment of a system in which the invention may be employed.

FIG. 2A schematically illustrates a first example implementation (denoted 100a) of a monitoring system 100 for monitoring one or more exercise machines. In this example only one exercise machine 1 is shown. However, it must be appreciated that the monitoring system would typically be arranged to monitor a plurality of exercise machines. The monitoring system 100a of FIG. 2A may comprise one repetition detector 10 and one exercise machine identifier 40 for each exercise machine that is to be monitored. The monitoring system 100a may further comprise a server 2, at least one observer 30, and a wireless communication device 50, a weight sensing device 60 and an admin tool 70. The server has access to a data storage 20.

Figure 2B:
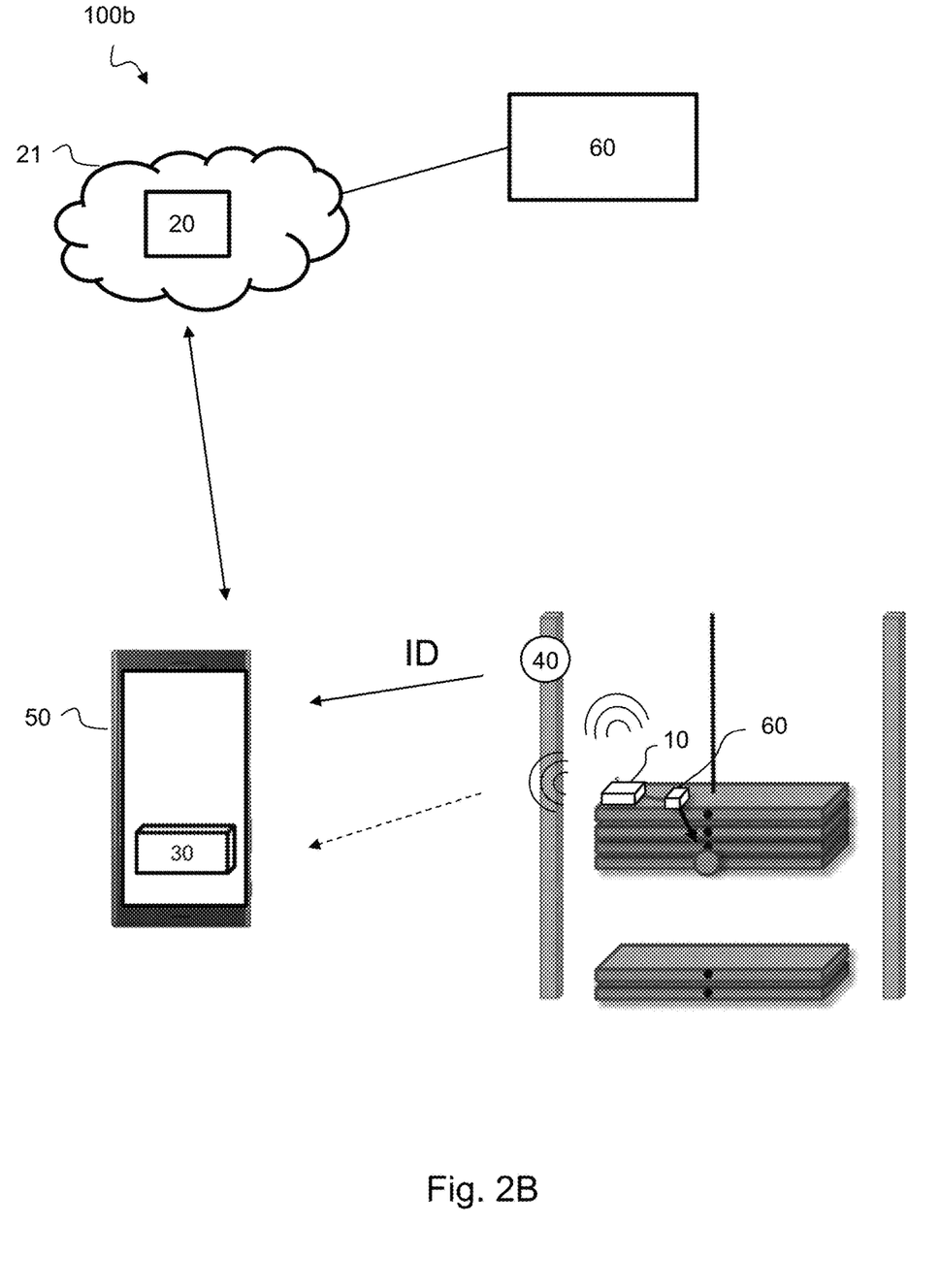
FIG. 2B illustrates a second example embodiment of a system in which the invention may be employed.

FIG. 2B illustrates a second example embodiment (denoted 100b) of the monitoring system 100. This embodiment differs from the first example embodiment in that the functionality of the observer 30 is integrated in the user device 50, for example the user's phone. This means that during exercise the signaling to from a server over internet is not needed.

The repetition detector 10, the exercise machine identifier 40 will be the same as in the first example embodiment. However, the functionality of the observer 30 and the user device 50 would typically be different, as no signaling there between is needed. In particular the observer 30 will provide the exercise data directly to the user device 50, as it is comprised therein. Furthermore, the user device 50 will be configured to, when occupied, broadcast a signal that informs other user devices that the exercise machine 1 is occupied.

Figure 3:
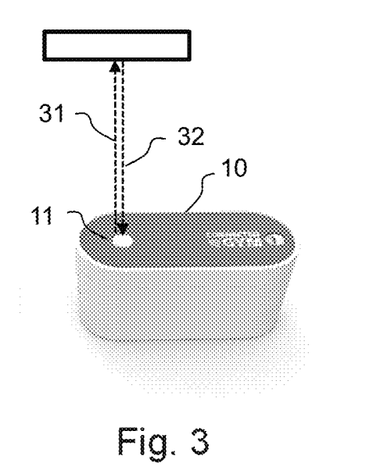
FIG. 3 illustrates an embodiment of a repetition detector of the system.
Figure 5A:
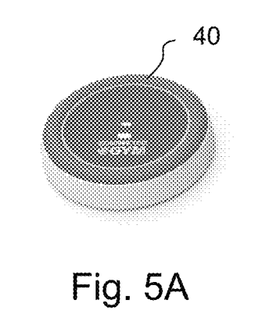
FIG. 5A illustrates an exercise machine identifier of the system.
Figure 5B:
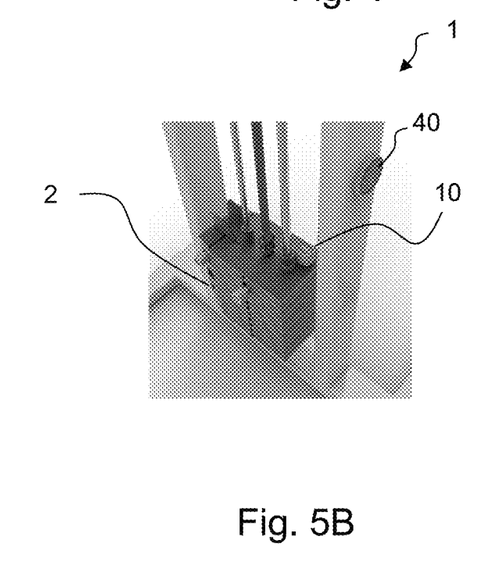
FIG. 5B illustrates the exercise machine identifier and the repetition detector when mounted.

FIG. 3 shows the repetition detector 10, also referred to as a main unit, in further detail. The repetition detector 10 is configured to be arranged to the stacked weights 2 of exercise machine 1. For example, it is configured to be arranged on the top of the stack of weights, for example on the uppermost weight, as shown in FIGS. 2A, 2B and 5B.

The repetition detector 10 may be configured to advertise information (for example a series of integers) associated with the exercising using short range wireless communication.

More specifically, the repetition detector 10 may comprise a sensor arrangement 11 configured to provide sensor data indicative of a longitudinal movement of at least one of the stacked weights 2. In exercise machines comprising stacked weights, the user may typically select how many of the weights should be used or engaged in the exercise. This is for example done by inserting a pin in one of the weights 2. During exercise the user will then indirectly "lift" the selected weights, which corresponds to a longitudinal movement of the selected weights. The training may be tracked by monitoring how many weights are selected to be lifted and how many times the selected weights are lifted.

In other words, the repetition detector 10 comprises a sensor arrangement 11 configured to detect when a user performs an exercise in the exercise machine 1, by detecting longitudinal movements (herein also referred to as repetitions) of at least one of the stacked weights 2. The sensor arrangement 11 may for example comprise an accelerometer, range finder, a tension meter and/or similar. In an example implementation the sensor arrangement 11 comprises a light range finder. The light range finder is configured to transmit a laser beam 31 and to receive a reflection 32 of the transmitted laser beam to determine the distance to a fixed point of the upper part of the exercise machine. For example, the rangefinder operates on the time of flight (TOF) principle by sending a laser pulse in a narrow beam towards the object and measuring the time taken by the pulse to be reflected off the target and returned to the sender.

Detection of a longitudinal movement of the stacked weight would then typically correspond to detecting that the distance between the repetition detector 10 and the exercise machine has changed a pre-determined amount, which corresponds to that the stacked weights 2 have been lifted. It is also possible to detect that at least one of the stacked weights 2 have moved more than a first pre-determined distance upwards, such as 2-5 cm, for determining that a first stroke is initiated, and/or a second predetermined distance, such as 10-70 cm from a rest position or from a lower pause position where the first stroke is initiated, before it starts moving in the opposite direction, for determining that a first half stroke has been carried out.

The repetition detector 10 may further comprise a short range wireless communication interface. The short range wireless communication interface for example uses Bluetooth Low Energy, BLE, ZigBee, LoRa.

The repetition detector 10 further comprises control circuitry configured to detect a longitudinal movement based on the sensor data provided by the sensor arrangement 11. The control circuitry is further configured to broadcast, using the short range wireless communication interface, a signal (such as an advertisement) comprising an identity of the exercise machine 1 and an indication of the detected longitudinal movement of at least one of the stacked weights 2. That the signal is broadcasted means that it may be heard by multiple receivers. Typically, it can be heard by an observer or user device that supports the short-range communication protocol. The broadcasted signal comprise may also comprise other data such as a sequence number and/or repetition number or other information.

For these type of applications low power consumption is crucial. Thus, in some embodiments the control circuitry is also configured to implement a power control function. The repetition detector 10 is then set in a sleep mode (which corresponds to practically completely switched off) when no exercise is performed, that is when the repetition detector 10 (and the stacked weights 2) is not moving or has not been moving for a predetermined period of time, such as 2-3 seconds. In various embodiments, the power control function is configured to set the repetition detector in sleep mode responsive to determining that the resistance member, for example the weight stack 2, has returned to a rest position and remained there for said predetermined period of time. An accelerometer or similar is then used to wake-up the repetition detector 10 when it starts moving, and may also be configured to detect an acceleration spike that indicates that the resistance member is returned to its rest position. The sensor arrangement 11 may be triggered by the accelerometer to start detecting repetitions. If the repetition detector 10 is still for more than a few seconds, it will return to sleep mode, for example, if it still for at least 2-3 seconds.

The detection and broadcasting are typically performed in real-time, such that each and every repetition that a user performs in the exercise machine is "reported". Thus, it is important that each and every signal can be correctly observed. Therefore, in one example implementation the broadcasted signal comprises a pulse-train of ten repeated signals.

Figure 7:
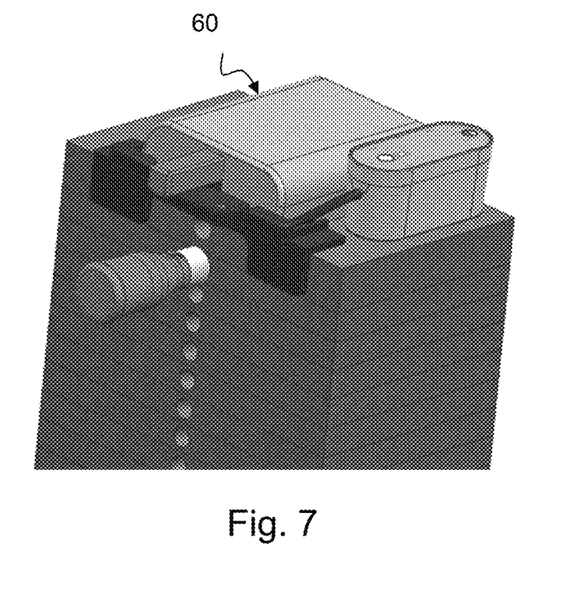
FIG. 7 illustrates a weight sensing device of the system.

In some embodiments, the repetition detector 10 also comprises or is connected to a weight sensing device 60 (FIG. 7) The weight sensing device 60 is configured to estimate the weight that the user uses when training. This may for example be implemented by measuring a distance between the weight sensing device 60 and an engaging member. One example implementation is shown in international patent application WO2017/178048. This may include sensing a distance between the device 60 and the weight pin 3, see FIG. 2, for example using a time of flight sensor in the weight sensing device 60. The position of the weight pin corresponds to the weight to be lifted, and the distance from the weight sensing device 60, positioned for example the top in the weight stack, to the weight pin 3 will then be proportional to the weight. Even in the event not all weights 2 in the stack are equal, they are still arranged in a predetermined order, and the measured distance can thus easily be transformed into a weight measurement. Where a weight sensing device 60 is included, the broadcasted signal may also comprise information about the estimated weight.

In conclusion, the at least one repetition detector 10 is configured to broadcast a short range wireless communication signal comprising an identity of the exercise machine 1 and an indication of a longitudinal movement of at least one of the stacked weights 2.

The exercise machine identifier 40, also referred to as a puck (FIG. 5A), may be configured to transmit a near field wireless communication signal comprising the identity of the exercise machine. More specifically, the exercise machine identifier 40 comprises a proximity detector for example a NFC receiver, configured to detect proximity of for example a user device 50 and a transmitter configured to transmit the near field wireless communication signal. The signal is for example NFC or RFID. The proximity detector and transmitter may be implemented by as an NFC tag. The near field wireless communication signal is typically received by a user device 50 (for example a user's smartphone). The user may then inform the server that he/she intends to start exercising in the exercise machine 1.

FIG. 5B illustrates the exercise machine identifier 40 and the repetition detector 10 when installed in the exercise machine 1. The repetition detector 10 is then mounted in the upper weight of the stacked weights 2.

The optional observer 30 (FIG. 4) comprises a short range wireless communication interface, for monitoring short range wireless communication signals transmitted by repetition detectors 10 arranged to a plurality of exercise machines in a gym. The observer 30 is configured to receive signals broadcasted by repetition detectors 10 and to generate exercise data based on the received signals. More specifically, the observer 30 parses the data from detected advertisements (for example a series of integers) and sends it on the server 21. The observer 30 typically doesn't know whether a user is registered or logged in at the machines, it just forwards all correctly parsed advertisements. This means that all training in the gym is tracked, even when the user is not registered to the service.

Figure 4:
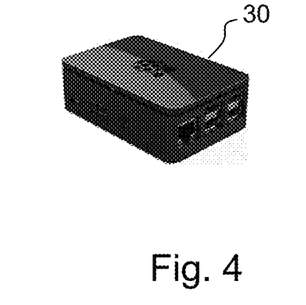
FIG. 4 illustrates an observer of the system.

Some analysis of the data is typically performed at the observer 30. More specifically, when the observer receives a pulse train from the repetition detector 10, then it filters the repetitions, for example removing duplicates having the same repetition number, and interprets it as one repetition. The generated exercise data is then forwarded to the server 21, where it is typically for stored in the data storage 20. The observer 30 for example uses ordinary internet communication for communication with the server 21. The observer 30 may also comprise logic for establishing such connection and to detect bad internet connection and to reconnect, when connection is lost.

The data storage 20 is configured to store the exercise data of the exercise machines. In this embodiment the data storage 20 is comprised in a server 21 or backend. Thus, the data storage 20 is for example a cloud implemented database or a remote database. The data stored in the data storage 20 may be used to gain insights and data about gym members and their training patterns and would also enable detailed analysis of utilization of gym machines.

The server 21 typically communicates over internet, for example using IP/Ethernet. The server 21 will receive exercise data from the observer and store it in the data storage 20. The stored exercise data can be used for all kinds of analysis at a later point in time. If a user device 40 is registered on a certain machine, then exercise data will be forwarded to the user device 50 in real time or substantially real time. In other words, exercise data corresponding to every detected repetition will be forwarded to the user device 50.

Figure 6:
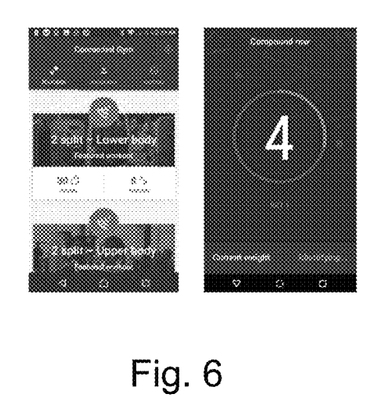
FIG. 6 illustrates a user interface of a user device.

The user device 50 is for example a smartphone comprising a mobile application, for example an android app (FIG. 6). In the mobile application the user may monitor machine training automatically in real-time, follow pre-defined workouts or save your personal workouts, view history of all training data, workout programs, statistics and progress.

The user device 50 is configured to receive the near field wireless communication signal from the exercise machine identifier 40. The user device 50 is configured to communicate with the server 21 and to retrieve exercise data from the server 21. The user device 50 may also inform the server 21 that it intends to start training in an exercise machine 1. In other words, the user device 50 is configured to register (log-in)/de-register (log-off) itself at the exercise machine 1.

When a user device 50 is registered at the exercise machine 1, the server 20 will then start forwarding exercise data to the user device in real-time. In other words, the user device 50 is configured to retrieve, from the server 21, exercise data corresponding to an exercise machine identity comprised in the received near field wireless communication signal.

The user device 50 will present exercise data or information associated therewith to the user in any form depending on implementation. For example, the weight, the number of repetitions and the exercise machine's name are displayed on a display of the user device 50. In other words, the user device 50 is configured to provide the retrieved exercise data to a user. After completion of the exercising the entire program is typically sent to the server 21 for storage.

The function and operation of the system according to various embodiments of the invention will now be described in further detail, with reference to the drawings, related to the example implementation setups of FIGS. 2A and 2B.

Figure 8:
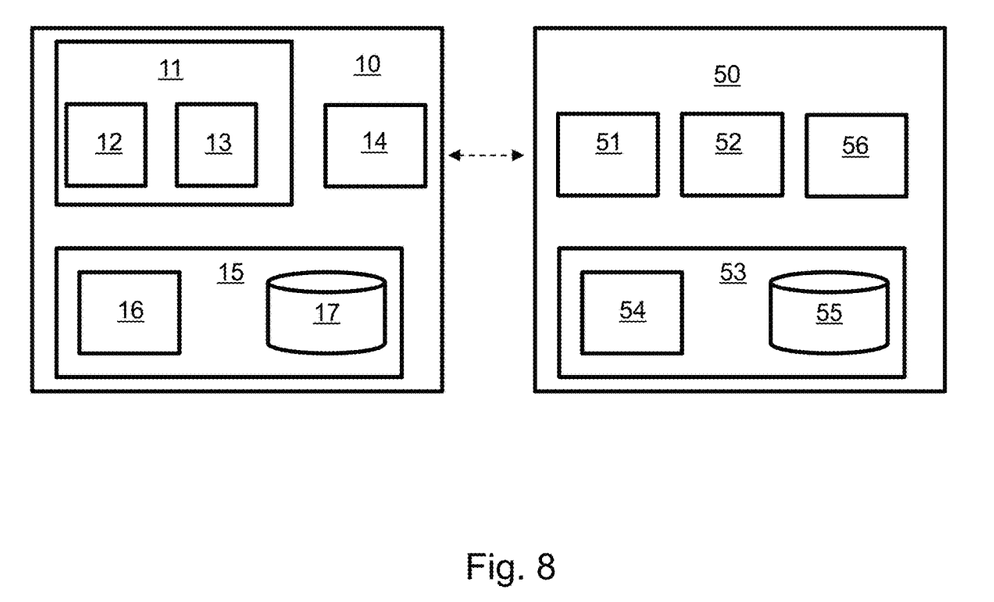
FIG. 8 illustrates an embodiment of a repetition detector and a user device communicating according to various methods as presented herein.

More specifically, various embodiments of the invention may be carried out in a system of FIG. 8. Herein, both the repetition detector 10 and a user device 50 are shown. The repetition detector 10 comprises a sensor arrangement 11, which is attachable to an exercise machine 1. The sensor arrangement may include one range meter 12 configured to sense a relative position, such as a relative position of a member of the exercise machine with respect to a reference position. The range meter may for example be a TOF sensor. The sensor arrangement 11 may further comprise an accelerometer 13, configured to detect movement of a member to which the accelerometer is attached, such as a part of the exercise machine. The repetition detector 11 further comprises control circuitry 15, comprising a processor 16 and memory storage 17 configured to hold program code which may be executed by the processor 16. The repetition sensor 10 further comprises a signal transceiver 14, operable to transmit for example sensor data. The transceiver 14 may for example be a short range wireless communication interface, as already exemplified. The repetition detector 10 further comprises a power source, such as a battery (not shown). While FIG. 8 shows the repetition detector as one unit, it may be pointed out that for example the range meter 12 and the accelerometer 13 need not be contained in a common casing. Indeed, these may be separate elements, configured to communicate separately to transmit sensor data, and receive trigger signals to perform sensing and to transmit sensed data.

FIG. 8 further shows a user device 50, such a mobile phone or small handheld computer, or even a combination of a wearable device, such as a wristlet, and a mobile phone or computer. The user device 50 comprises a data receiver 51, for example a data transceiver, for at least receiving signals and data from the repetition detector 10. A further transceiver 52 may be included for communicating through another air interface, such as a cellular access technology and/or a wireless LAN access technology. The user device 50 comprises control circuitry 53 including logic configured to carry out method steps as outlined herein. The control circuitry may include a processor 54 and memory storage 55, wherein the processor 54 is configured to execute program code stored in said memory storage 55 to generate said logic. Herein, the memory storage 55 will also be referred to for storing both data and algorithms usable for making calculations according to various embodiments. However, it may be noted that such data and algorithms may be stored in different physical media than the program code and may even be stored in cloud storage, accessible by means of for example the transceiver 52. The user device 50 may further comprise a display 56, or alternatively a communication interface to an external display, for example provided on the exercise machine 1.

As noted, users of exercise machines often perform the exercise motion too quickly or too slowly or with an inconsistent repetition speed. The result may be that the desired effect of the training is not obtained, and that the risk of injury may increase. For these reasons, users may need a guide to help them do the movement accurately. Gym staff and personal trainers may be consulted, but it is oftentimes not feasible to employ a personal trainer for each exercise session. The embodiments presented herein are based on an alternative solution, wherein the user is guided by means of an indicator out put on a display 56, representing a certain period or frequency for carrying out the exercise motion. In various embodiments, the indicator may include an animation, such as an object pulsating or moving according to said period, as will be described further below by means of an example embodiment with reference to FIGS. 9A through 9G and 10.

Figure 11:
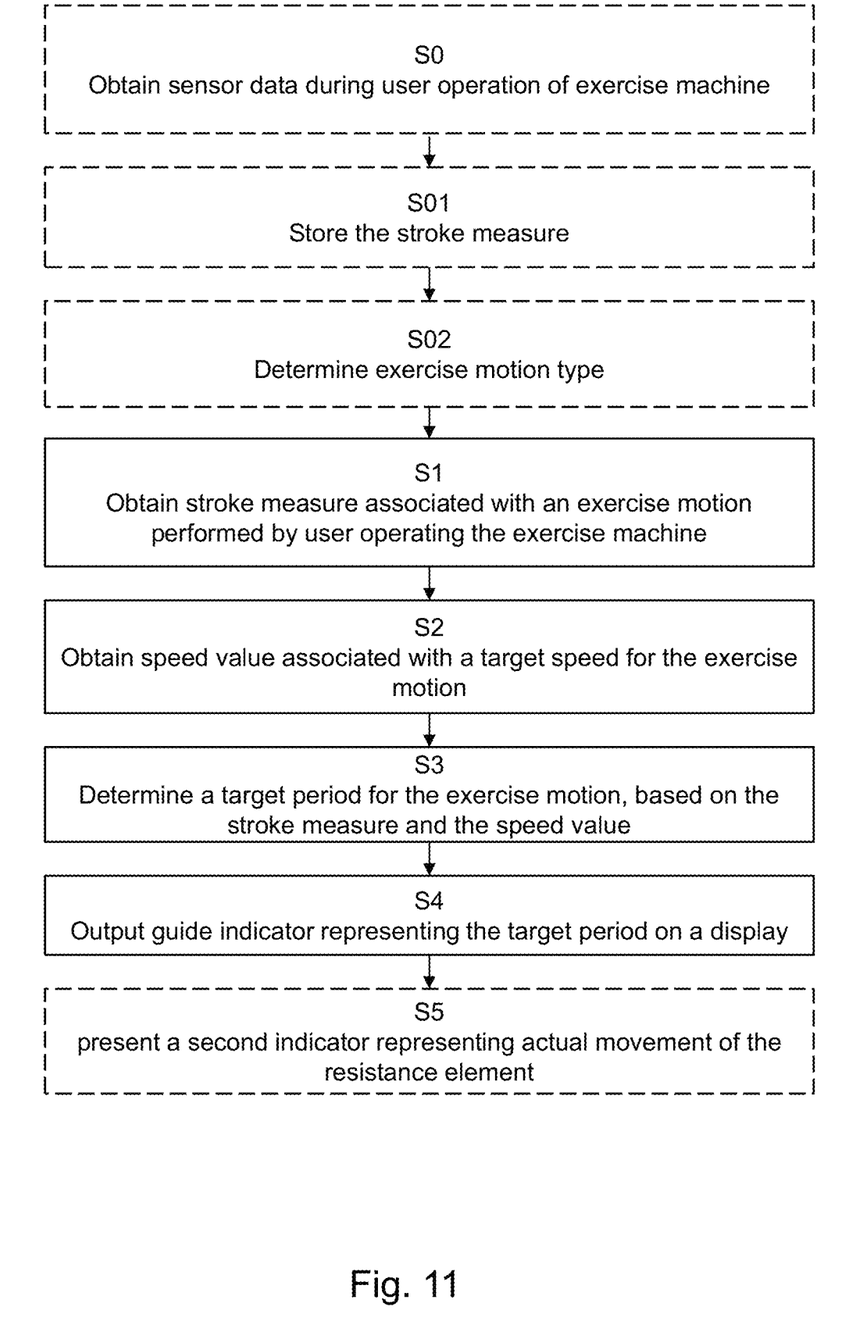
FIG. 11 illustrates a method for enhancing user operation of an exercise machine according to various embodiments.

Various embodiments will now be described with reference to FIG. 11.

In a step S1, a stroke measure x associated with an exercise motion performed by user operating the exercise machine is obtained. Herein, the stroke is referred to as a distance between outermost positions of the exercise motion, measured between two positions of the exercise machine, such as the difference between the summit and the valley of the weight stack as it moves up and down. It may for example relate to the relative position of the uppermost weight of the weight stack 2, or a lifting mechanism, with respect to for example the floor or a static part of the exercise machine. The outermost positions may include a first position, a start position, from which the user starts pulling/pushing a handle of the exercise machine, and a second position, an end position, at which the user stops pulling/pushing and starts releasing.

In various embodiments, the stroke measure x may be determined by means of sensor data from the repetition detector 10, in a step S0. The end positions may relate to positions where the acceleration, as determined by the accelerometer 13, has a maximum absolute value throughout the motion. In some embodiments, the outermost positions may be determined directly by the range meter 12, which may be configured to intermittently measure a relative position during the motion.

In various embodiments, the stroke measure x is determined in the repetition detector 10, based on the sensor data, and transmitted to the user device 50 for obtainment. In other embodiments, sensor data from the sensor arrangement 11 is transmitted to the user device 50, in which the stroke measure x is determined based on the sensor data.

In some embodiments, the stroke measure x may be determined at one event when the user operates the exercise machine, whereupon the stroke measure x is stored in a step S01. Storing may be made in memory storage 55 of the user device 50. Alternatively, it may be stored in the cloud, where it may later be retrieved by the user device 50. In such embodiments, the step S1 of obtaining the stroke measure x, at another instance of using the exercise machine, may thus be accomplished by retrieving the stroke measure x from memory, rather than measuring it again. This stroke measure x retrieval may be trigger by the user logging in with the exercise machine using the user device 50 and the exercise machine identifier 40.

In various embodiments, either step S0 or step S01 may be included at an instance of using the exercise machine in accordance with the invention, whereas the other step is optional. In other words, these steps define different embodiments for determining the stroke measure x obtained in step S1.

For exercise machines that may be operated for different types of exercise motions, the user device may be operated to select the motion in question to perform in a step S02, for example using a user interface of the user device 50. Where the stroke measure x is retrieved from memory, this user input may also control which stroke measure data to obtain by data retrieval.

In a step S2, a speed value v associated with a target speed for the exercise motion is obtained. The target speed value v may for example be set or determined by the user or with help of a personal trainer and is selected to obtain a certain desired effect with the exercise. Various different target speeds may thus be usable for the same exercise machine, dependent on the type of training to do. Obtainment of the speed value v may be performed by retrieving the value from data storage 55 in the user device 50, from a remote cloud storage, or from local storage at the gym, using the user device 50. The speed value v can be determined in the direction of the stroke distance x, and is thus in reality a measure of velocity.

In a step S3, a target period T1 for the exercise motion is determined, based on the stroke measure x and the speed value v. In this context, the period T1 relates to the cycle time of an exercise motion, such as from a first end position to a second end position and back to the first end position. The period T1 is thus the inverse of the repetition frequency.

In various embodiments, the period T1 is determined by calculation in the user device 50, wherein the period T1 is proportional to the stroke measure x and inversely proportional to the determined speed value v. In some embodiments, the determination is made under the approximation of a sinus curve, which as such represents a motion which is slower at the top and bottom, in other words the end positions where the motion turns direction, and fast in the middle. In various embodiments, the target speed, or velocity, is defined as the maximum speed during the motion. In such an embodiment, the time period T is determined as $T1=pi*x/v$. In other embodiments, a first speed value v1 may be associated with a first target speed from a first end position to a second end position of the exercise motion, and a second speed value v2 may be associated with a second target speed from the second end position to the first end position of the exercise motion. This may for example relate to a motion with a fast pulling/pushing action, followed by a slower release back to the starting position. In such an embodiment, the target period T2 may include a first period portion T21 based on the stroke measure and the first speed value v1, for example based on a sinus shape as before or even a constant speed determined as $T21=x/v1$. A second period portion T22 may correspondingly be based on the stroke measure x and the second speed value v2, determined as a sinus or constant speed movement. The total period T2 thus includes the sum of T21 and T22. The total period T2 may further include an idle rest period T23 between T21 and T22; that is $T2=T21+T22+T23$.

In a step S4, a guide indicator representing the target period T1 is output on a display 56. In various embodiments, the guide indicator is controlled to oscillate with the determined period T1. Test shows that people are very good at following such an animation.

In an optional step S5, the logic of the user device 50 may be configured to present a second indicator representing actual movement of the resistance element based on sensor data from the sensor arrangement 11, such as position data determined by means of the range meter 12. This may be helpful for understanding how well the user is able to follow the guide indicator showing the target period T1 or T2. In some embodiments, the second indicator may instead, or additionally, include text feedback, or audible feedback, based on how well the user following the guide indicator, such as "good job", "slow down", "speed up" etc.

Animations usable in steps S4 and S5 will now be described by way of example with reference to FIGS. 9A through 9G and 10. Each drawing shows a representation of a user interface presentable on a display 56. In the user interface, end positions of the exercise motion are indicated by concentric circles 91 and 92: a static inner circle 91 marks a first end position of the exercise motion, and a static outer circle 92 marks the second end position of the exercise motion. The guide indicator 93 includes an animation of a circle controlled to change radius with the determined period, for example T1, between an inner radius limit of circle 91 and an outer radius limit of circle 92.

FIGS. 9A through 9G and 10 shows a guide indicator in various phases of a set including four repetitions. The repetition number may be presented by a number in the inner circle, as illustrated. Moreover, a completion indicator 94 may be presented, which indicates to the user how far into the set the user has reached. The completion indicator may be presented as a circumference portion 94 outside of the outer circle 92. Since this example includes a set of four repetitions, the completion indicator indicates a fourth of the entire circumference as long as the first repletion is carried out. In an alternative embodiment, the completion indicator 94 may rather indicate that a certain repetition is completed after it is finished.

Start of an exercise motion may be determined using the sensor arrangement 11. In many types of exercise motions using an exercise machine 1, a lower end position is not a rest position of the resistance element, such as a weight stack 2. Rather, the weight stack is normally raised a portion to assume a first, lower, end position of the motion, then raised to the second end position and released back to the first position. The weight stack is subsequently let down to the rest position again when the set is completed.

In one embodiment, the sensor arrangement is configured to detect initiation of a motion using the accelerometer 13. The accelerometer will yield a signal over a predetermined threshold associated with an acceleration value when the user first lifts the weight stack. This may trigger the range meter 12 to measure its relative position, for example once or a number of intermittent times. If the detected relative position exceeds a position threshold value from a rest position, such as at least 2-5 cm, it may be determined that the user is initiating a stroke of an exercise motion. In such an embodiment, the range meter is triggered to intermittently, such as 5-10 times a second, measure its relative position to sample position data, based on which the distance x may be determined. If, on the other hand, the detected relative position does not exceed the position threshold value from a rest position, it may be determined that the detected acceleration was caused by other reasons, such as by accident or by the user making adjustments to the exercise machine 1. This causes the range meter to stop measuring its relative position, and thereby to save battery. The determination that the user is initiating a stroke of an exercise motion may also involve time, using a clock function in the repetition detector 10, wherein the position threshold value must be exceeded at least a predetermined time period from triggering by the accelerometer, for example 2-5 seconds, or else the range meter is configured to stop measuring its relative position to save battery energy.

Figure 9A:
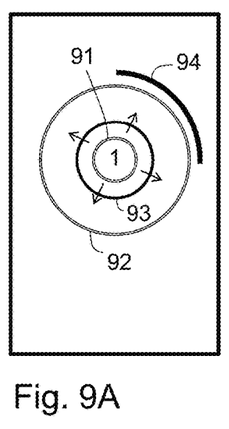
FIGS. 9A through 9G illustrates an animation provided on a user interface of the user device according to various embodiments.
Figure 9B:
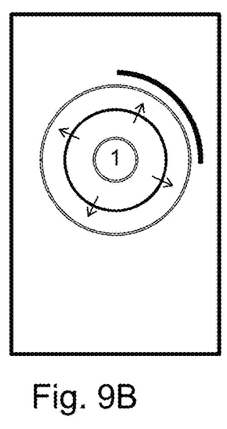
Figure 9C:
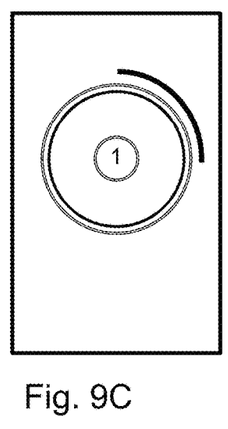

In FIGS. 9A-9C, the first repetition is initiated, and the guide indicator 93 starts expanding from the inner limit 91 towards the outer limit 92. Note that the arrows in these drawings merely indicate the direction of motion of the guide indicator 93, and not as objects presented on the user interface.

Figure 9D:
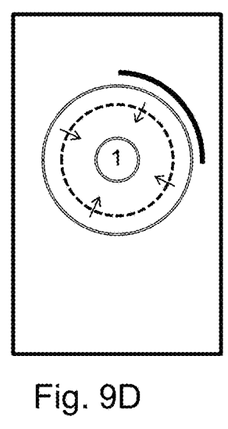
Figure 9E:
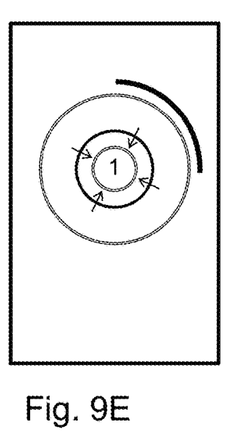

In FIGS. 9D-9E, after reaching the outer limit 92 in FIG. 9C, the guide indicator 93 starts retracting towards the inner limit 91.

Figure 9F:
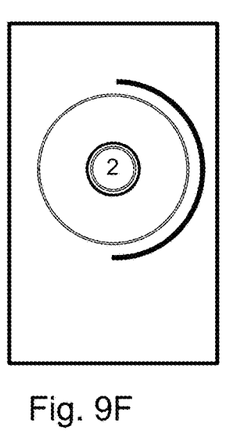

In FIG. 9F, the guide indicator has reached the inner limit 91, and marks that the first repetition is completed. This may involve increasing the center indicator from 1 to 2, and may also involve updating the completion indicator 94 to indicate that the user is now performing the second out of four repetitions.

Figure 9G:
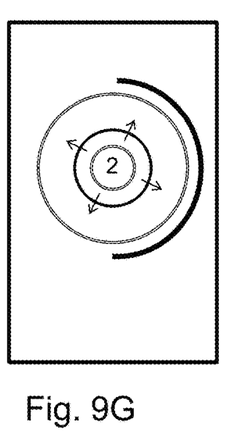

In FIG. 9G, animation associated with the second repetition commences, in the same manner as for the first repetition ion FIG. 9A.

In various embodiments, the first detected completed stroke may be used for determining the distance x, wherein the distance x is obtained by measuring the difference of the relative position of the detected end positions when operating the machine 1. In such an embodiment, the guide indicator 93 may either be absent during the first stroke, or alternatively be shown with a nominal time period value Tn calculated based on a nominal stroke distance xn. After the first stroke is completed, the period T may be obtained based on the measured distance x, and subsequently employed for showing the animation of the guide indicator 93.

Figure 10:
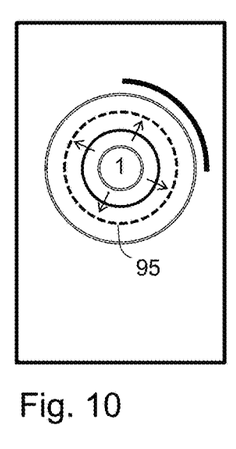
FIG. 10 illustrates a variant o the animation provided on a user interface.

FIG. 10 illustrates an embodiment corresponding to FIG. 9A. Herein, though, and additional second indicator 95 is shown, representing the actual motion of the user, for example actual movement of the resistance element based on detected position data. In such an embodiment, rather than just determining a suitable period and assisting the user in controlling the exercise machine 1 by means of guide indicator 93, the user's success in following the guide indicator 93 is presented. When the exercise motion is performed as intended, the second indicator 95 will overlap the guide indicator. In various embodiments, the second indicator 95 is only presented if and when the user fails to follow the guide indicator to a certain predetermined degree, for example when a calculated actual speed of motion deviates from the target speed v to a certain extent, such as a delta value or a percentage value. In some embodiments, the second indicator is configured to change color dependent on correlation with the guide indicator. For example, if the motion is performed too fast the second indicator may be presented with a first color, such as yellow, and if the motion is too slow the second indicator may be presented with a second color, such as red. In some embodiments, both the first and second colors deviate from a color of the guide indicator, which for example may be green.

In the drawings and specification, various aspects of the disclosure have been disclosed. However, many variations and modifications can be made to these aspects without substantially departing from the principles of the present disclosure. Thus, the disclosure should be regarded as illustrative rather than restrictive, and not as being limited to the particular aspects discussed above. Accordingly, although specific terms are employed, they are used in a generic and descriptive sense only and not for purposes of limitation.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatus, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

The various example embodiments described herein are described in the general context of method steps or processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that performs particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Various embodiments of the proposed solutions may include any combination of the following clauses C:

C1. A device configured to enhance user operation of an exercise machine, the device comprising
control circuitry including logic configured to
obtain a stroke measure associated with an exercise motion performed by the user operating the exercise machine;
obtain a speed value associated with a target speed for the exercise motion;
determine a target period for the exercise motion, based on the stroke measure and the speed value;
output a guide indicator representing the target period on a display.

C2. The device of C1, comprising a data receiver configured to receive said stroke measure from a sensor arrangement of the exercise machine.

C3. The device of C1, a data receiver configured to receive position data of a resistance element of the exercise machine from a sensor arrangement, wherein the logic is configured to determine the stroke measure based on said position data.

C4. The device of any preceding clause, wherein said stroke measure is a measured distance between two end positions of said exercise motion.

C5. The device of any preceding clause, comprising
a memory for storing said stroke measure.

C6. The device of C5, wherein the logic is configured to obtain the stroke measure from said memory.

C7. The device of any preceding clause, comprising said display.

C8. The device of any preceding clause, wherein said control circuitry includes
a processor; and
memory storage;
wherein the processor is configured to execute program code stored in said memory storage to generate said logic.

C9. The device of any preceding clause, wherein said guide indicator is controlled to oscillate with the determined period.

C10. The device of any preceding clause, wherein said guide indicator includes an animation of a circle controlled to change radius with the determined period between an inner radius limit and an outer radius limit.

C11. The device of C9 or C10, wherein said guide indicator is controlled to present a repetition indication, associated with a number of repetitions of the exercise motion carried out in one set of repetitions.

C12. The device of any preceding clause, wherein the target speed represents a predetermined desired maximum speed between end position of the exercise motion.

C13. The device of any preceding clause, wherein the target period (T1), representing the exercise motion from a first end position to a second end position and back to the first end position is determined as $T1=pi*x/v$, where x is the stroke measure and v is the target speed.

C14. The device of any preceding C1-12, wherein the logic is configured to
obtain a first speed value (v1) associated with a first target speed from a first end position to a second end position of the exercise motion, and obtain a second speed value (v2) associated with a second target speed from the second end position to the first end position of the exercise motion,
wherein said target period includes a first period portion based on the stroke measure and the first speed value, and a second period portion based on the stroke measure and the second speed value.

C15. The device of C14, wherein said target period includes an idle period between the first period portion and the second period portion.

C16. The device of C3, wherein the logic is configured to present a second indicator representing actual movement of the resistance element based on said position data.

C17. A system configured to enhance user operation of an exercise machine, comprising
a device according to any of the preceding clauses; and
a sensor arrangement connectable to the exercise machine, including
an accelerometer to sense acceleration during an exercise motion, and
a range meter to sense a relative position of a member of the exercise machine;

a sensor controller configured to output data based on sensed data to the device.

C18. The system of C17, wherein the stroke measure is a distance between two sensed relative end positions of said exercise motion.

C19. The system of C17 or 18, wherein the sensor arrangement is configured to detect initiation of a motion using the accelerometer;
detect a relative position using the range meter responsive to detected initiation;
determine start of a stroke responsive to the detected relative position exceeding a threshold value from a rest position.

C20. A method carried out in a user device for enhancing user operation of an exercise machine, comprising obtaining a stroke measure associated with an exercise motion performed by the user operating the exercise machine;
obtaining a speed value associated with a target speed for the exercise motion;
determining a target period for the exercise motion, based on the stroke measure and the speed value;
outputting a guide indicator representing the target period on a display.

C21. The method of C20, including any of the steps carried out by the user device in C1-C16.

The invention claimed is:

1. A device configured to control user operation of an exercise machine, comprising:
    a control unit including logic configured to:
        obtain a stroke measure associated with an exercise motion performed by the user operating the exercise machine, wherein said stroke measure is a distance between two end positions of said exercise motion measured during operation by the user;
        obtain a speed value associated with a target speed for the exercise motion, wherein the target speed represents a predetermined maximum speed between end positions of the exercise motion;
        determine a target period for the exercise motion, based on the stroke measure and the speed value, wherein the target period (T1), representing the exercise motion from a first end position to a second end position and back to the first end position is determined as T1=pi*x/v, where x is the stroke measure and v is the target speed; and
        output a guide indicator representing the target period on a display.

2. The device of claim 1, comprising a data receiver configured to receive position data of a resistance element of the exercise machine from a sensor arrangement, wherein the logic is configured to determine the stroke measure based on said position data.

3. The device of claim 2, wherein the logic is configured to present a second indicator representing actual movement of the resistance element based on said position data.

4. The device of claim 1, wherein said guide indicator is controlled to oscillate with the determined target period.

5. The device of claim 4, wherein said guide indicator is controlled to present a repetition indication, associated with a number of repetitions of the exercise motion carried out in one set of repetitions.

6. The device of claim 1, wherein the logic is configured to:
    obtain a first speed value (v1) associated with a first target speed from a first end position to a second end position of the exercise motion, and
    obtain a second speed value (v2) associated with a second target speed from the second end position to the first end position of the exercise motion,
    wherein said target period includes a first period portion based on the stroke measure and the first speed value, and a second period portion based on the stroke measure and the second speed value.

7. The device of claim 6, wherein said target period includes an idle period between the first period portion and the second period portion.

8. The device of claim 1, comprising a data receiver configured to receive said stroke measure from a sensor arrangement of the exercise machine.

9. The device of claim 1, comprising a memory for storing said stroke measure.

10. The device of claim 1, comprising said display.

11. The device of claim 1, wherein said control unit comprises:
    a processor; and
    memory storage;
    wherein the processor is configured to execute program code stored in said memory storage to generate said logic.

12. The device of claim 1, wherein said guide indicator includes an animation of a circle controlled to change radius with the determined target period between an inner radius limit and an outer radius limit.

13. A system configured to control user operation of an exercise machine, comprising:
    a device having a control unit and a display;
    a sensor arrangement connectable to the exercise machine, including:
        an accelerometer to sense acceleration during an exercise motion, and
        a range meter to sense a relative position of a member of the exercise machine; and
    a sensor controller configured to output data to the device, the data that is output is based on data that is sensed by the sensor arrangement;
    the control unit including logic configured to:
        obtain a stroke measure from the sensor arrangement associated with an exercise motion performed by the user operating the exercise machine, wherein said stroke measure is a distance between two end positions of said exercise motion measured during operation by the user;
        obtain a speed value associated with a target speed for the exercise motion, wherein the target speed represents a predetermined maximum speed between end positions of the exercise motion;
        determine a target period for the exercise motion, based on the stroke measure and the speed value, wherein the target period (T1), representing the exercise motion from a first end position to a second end position and back to the first end position is determined as T1=pi*x/v, where x is the stroke measure and v is the target speed; and
        output a guide indicator representing the target period on the display.

14. The system of claim 13, wherein the sensor arrangement is configured to:
    detect initiation of a motion using the accelerometer;
    detect a relative position using the range meter responsive to detected initiation; and
    determine start of a stroke responsive to the detected relative position exceeding a threshold value from a rest position.

15. A method carried out in a user device for controlling user operation of an exercise machine, comprising:
- obtaining a stroke measure associated with an exercise motion performed by the user operating the exercise machine, wherein said stroke measure is a distance between two end positions of said exercise motion measured during operation by the user;
- obtaining a speed value associated with a target speed for the exercise motion, wherein the target speed represents a predetermined maximum speed between end positions of the exercise motion;
- determining a target period for the exercise motion, based on the stroke measure and the speed value, wherein the target period (T1), representing the exercise motion from a first end position to a second end position and back to the first end position is determined as T1=pi*x/v, where x is the stroke measure and v is the target speed; and
- outputting a guide indicator representing the target period on a display.

* * * * *